US010716532B2

(12) United States Patent
Sumner

(10) Patent No.: US 10,716,532 B2
(45) Date of Patent: Jul. 21, 2020

(54) PROTECTIVE CASE FOR STETHOSCOPE CHESTPIECE

(71) Applicant: Gregory Faris Sumner, Altamonte Springs, FL (US)

(72) Inventor: Gregory Faris Sumner, Altamonte Springs, FL (US)

( * ) Notice: Subject to any disclaimer, the term of this patent is extended or adjusted under 35 U.S.C. 154(b) by 407 days.

(21) Appl. No.: 15/904,318

(22) Filed: Feb. 24, 2018

(65) Prior Publication Data

US 2018/0263592 A1 Sep. 20, 2018

Related U.S. Application Data

(60) Provisional application No. 62/472,016, filed on Mar. 16, 2017.

(51) Int. Cl.
*A61B 7/02* (2006.01)

(52) U.S. Cl.
CPC ..... *A61B 7/02* (2013.01)

(58) Field of Classification Search
CPC ..... A61B 7/02; A61B 50/30
USPC ..... 181/131
See application file for complete search history.

(56) References Cited

U.S. PATENT DOCUMENTS 3,213,960 A * 10/1965 Wagner ..... A61B 7/02 181/126
3,766,361 A * 10/1973 Swinyar ..... A61B 7/02 219/521
3,797,717 A * 3/1974 Collins ..... A45C 11/00 224/231
5,171,087 A * 12/1992 Green ..... A61B 7/02 219/242
5,172,683 A * 12/1992 West ..... F24V 30/00 126/263.05
5,692,657 A * 12/1997 Kilo ..... A45F 5/02 181/131
5,892,233 A * 4/1999 Clement ..... A61L 2/10 181/131
D425,353 S * 5/2000 Foy ..... D24/134

(Continued)

OTHER PUBLICATIONS

Screen shot of "Three Mitten Medical Professional Stethoscope Holders with Scrub-Lock" on Amazon.com. Published internationally. Publication date not known.

(Continued)

*Primary Examiner* — Jeremy A Luks
(74) *Attorney, Agent, or Firm* — John V. Stewart

(57) ABSTRACT

A protective case in two parts (L, R) interconnected by a flexible top wall (28) acting as a hinge and a closure spring. Opposed jaws (32, 34) in the two respective parts (L, R) hold a stethoscope chestpiece (40) within the case, and protect its diaphragm (43) behind a separable (24) front wall (22). The jaws have insertion ramps (33A, 35A) that open the jaws upon insertion of the chestpiece, a retention portion (33C, 35C), and removal ramps (33D, 35D) that open the jaws upon removal. A chest piece is inserted by pushing it into the insertion ramps. It is removed by pulling it outward against the removal ramps. This protects the chestpiece from damage in a medical equipment bag to which the case may be attached by a lanyard (37) for quick location. A back wall (23) may protect a second diaphragm (45) of the chestpiece.

12 Claims, 3 Drawing Sheets

20A
26
28
30
6
27
25
24
22
8.5 X 11
R
L
6

(56) References Cited

U.S. PATENT DOCUMENTS

| | | | | |
|---|---|---|---|---|
| 6,419,133 | B1 * | 7/2002 | Grose | A61B 7/02<br>224/269 |
| 6,484,918 | B1 * | 11/2002 | Lefebvre | A45F 5/02<br>181/131 |
| 7,036,627 | B2 * | 5/2006 | Costa | A61B 7/02<br>181/131 |
| 10,271,815 | B2 * | 4/2019 | Carallo | A61B 7/00 |
| 2011/0010822 | A1 * | 1/2011 | Singer | A61B 5/6806<br>2/161.7 |
| 2019/0247007 | A1 * | 8/2019 | Tsai | A61B 50/30 |

OTHER PUBLICATIONS

Screen shot of "Convenient Hat Stethoscope Protection" on Amazon.com. Published internationally. Publication date not known.

* cited by examiner 20A
27
28
25
22
24
L
R 20A
26
6
28
30
27
25
24
22
8.5 X 11
L
R
6

20A
22
24
38
L
R
39
30
32A
34A
32B
34B
32
23
26
34

20A
32B
32A
23
22
24
30
26
44
42
43
34A
34B
45
46
40

20A
32B
32A
43
23
22
45
24
26
40
34A
34B

PROTECTIVE CASE FOR STETHOSCOPE CHESTPIECE

CROSS-REFERENCE TO RELATED APPLICATIONS

This application claims the benefit of U.S. provisional patent application 62/472,016 filed Mar. 16, 2017, which is incorporated herein by reference in its entirety.

FIELD OF THE INVENTION

The invention relates to protection of a stethoscope chestpiece. More particularly, it relates to protecting a stethoscope chestpiece from forces and contamination encountered especially while stored or carried with other equipment and while carried by a practitioner.

BACKGROUND

The stethoscope is an important device utilized in a wide variety of medical fields. All of the components of a stethoscope are traditionally constructed in a way, and of materials, that are durable and rarely, if ever, replaced or repaired, except for the diaphragm. The diaphragm is a thin membrane, traditionally made of plastic, that is placed across the bell of the stethoscope chestpiece and used to collect the sound that is conveyed through the other components of the stethoscope and eventually auscultated (heard) through the ear pieces. It's the diaphragm's necessarily thin design that makes it vulnerable to damage from tactile forces. In most uses the tactile forces the diaphragm encounters are appropriate and cause no damage. The problem arises when the stethoscope is stored in storage bags, boxes, cases, etc. with a variety of, but not limited to, other medical devices. When stored in these situations without external protections, the diaphragm is exposed to tactile forces that can, and often do, damage it. The damage can reduce the effectiveness of the diaphragm, or render it completely ineffective and requiring it to be replaced. There are protective cases commercially available that will effectively protect all of the stethoscope's components. These cases are bulky, cumbersome and/or time consuming to use in certain situations.

Replacement diaphragms are relatively inexpensive and, in most cases, can be replaced in just a few minutes. For most medical professionals this is a minor, occasional annoyance, but, for some, this otherwise minor annoyance poses a substantial hindrance to the performance of their duties. The medical professionals that are most negatively affected are emergency medical workers. These emergency medical workers include Emergency Medical Technicians (basic, intermediate and paramedic), doctors, nurses and other first responders. These professionals often work in high-stress, fast-paced and often dangerous environments. Emergency workers need quick and easy access to their equipment and for that equipment to work properly every time. As this relates to stethoscopes, they are needed for numerous time sensitive medical evaluations. Due to this often urgent need, stethoscopes are commonly stored in larger storage devices alongside various other equipment. This equipment can, and often does, include devices and supplies that can damage the diaphragm of the stethoscopes. To protect the stethoscope from this damage the only viable option is to utilize the previously mentioned bulky, cumbersome and time consuming cases. These cases can hinder emergency medical workers from performing critical evaluations in a timely manner. Due to this cumbersome process, these protective cases are commonly not utilized and the stethoscope diaphragm is left vulnerable to damage.

If the stethoscope diaphragm is found damaged on a scene where its use is required for a medical evaluation, the emergency worker might attempt to use the stethoscope in the damaged, less effective state, try to find another stethoscope or forgo the evaluation all together. The emergency workers will almost never attempt to replace the diaphragm due to the time, equipment and supplies necessary to complete the repair.

SUMMARY OF INVENTION

An object of the invention is a case that protects a stethoscope chestpiece from damage while carrying the stethoscope and when storing it with other articles. Another object is a case that can be instantly located and instantly attached to or removed from the chestpiece. Another object is small size, not needing to enclose a whole stethoscope to protect the chestpiece. Another object is low cost, with an option of manufacturing the case from a single plastic injection mold. Another object is a case that can be worn around the neck of a practitioner or attached by a lanyard to a medical practitioner's bag.

DRAWINGS

DETAILED DESCRIPTION

Figure 2:
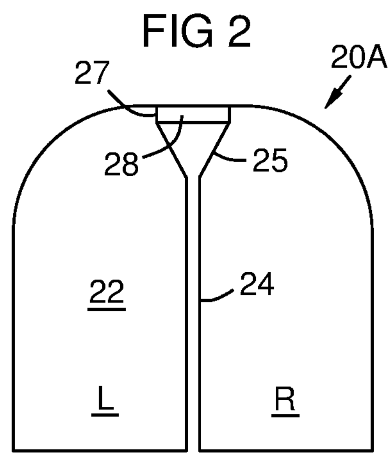
FIG. 2 is a front view of the case of FIG. 1.
Figure 1:
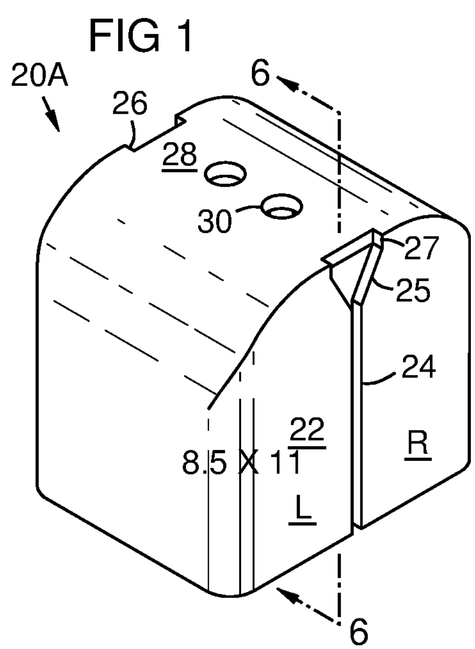
FIG. 1 is an isometric top/front/side view of a protective case in accordance with aspects of the invention.

FIG. 1 shows a protective case 20A having a front wall 22 with a separation slot 24 that allows the case to flexibly open and close around the stethoscope chestpiece as later shown. The back wall (not visible) also has a separation slot 26 partially seen. The front and back walls and slots may be mirror images of each other. The top wall 28 is made of a springy material such as semi-rigid plastic so that the left and right halves L, R of the case elastically diverge to receive the chestpiece, then close and hold it under spring force. The whole case may be made of the same material, and may be manufactured by injection molding or 3-D printing. One or more holes 30 may be provided in the top of the case for a lanyard as later described. Internal jaws may be shaped as later shown to allow the chestpiece to be quickly removed from the case by pulling the stethoscope outward while retaining the lanyard as in FIG. 6D. The lanyard may be attached to a medical bag in which the stethoscope is stored and carried. The top end of the slot 24 may be enlarged 25 to allow a span of the top wall 28 to flex with reduced stress concentration. The enlargement 25 may be in the shape of a base-up triangle as shown, or other shapes. It may include a reduction 27 of the top wall 28, making the top wall more flexible, or it may stop at the top wall. Although the slot is shown with sharp edges for clarity, the edges may be rounded. FIG. 2 is a front view of the case 20A of FIG. 1.

Figure 3:
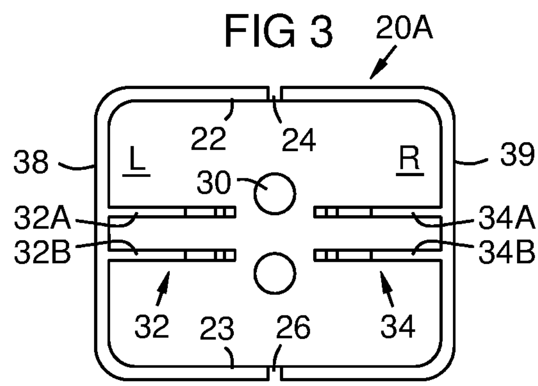
FIG. 3 is a bottom view of the case of FIG. 1.

FIG. 3 is a bottom view of the case 20A, showing front and back walls 22, 23, with respective front and back wall separation slots 24, 26. Left and right clamp jaws 32, 34 may be formed inside the case from one or more fins 32A, 32B attached to the left wall 38 of the case, and one or more fins 34A, 34B attached to the right wall 39 of the case.

Figure 4:
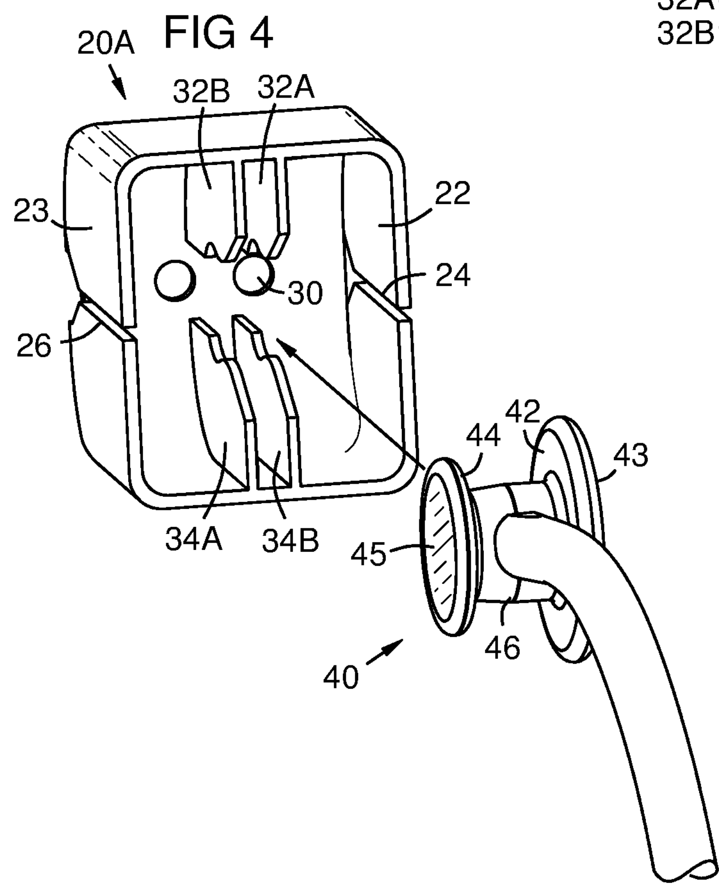
FIG. 4 is a perspective bottom/back view of the case of FIG. 1 with an approaching stethoscope chestpiece.
Figure 5:
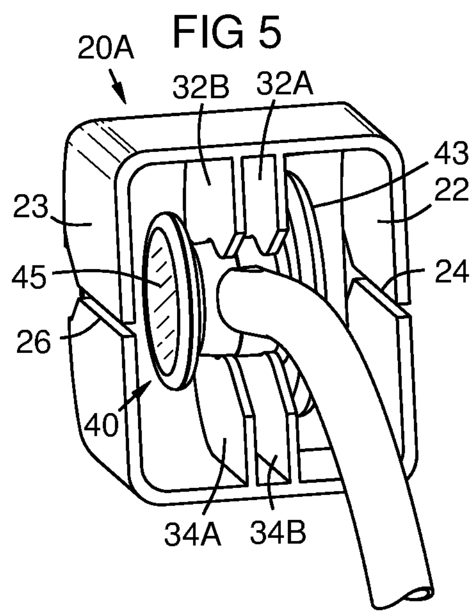
FIG. 5 is the view of FIG. 4 with the chestpiece inserted into the case.

FIG. 4 is a bottom perspective view of the case 20A with an approaching stethoscope chestpiece 40. Some stethoscopes have two opposed bells 42, 44 of different sizes for adult and pediatric patients and/or for high/low frequencies. The bells are attached to a body 46 of the chestpiece. One or both bells may have diaphragms 43, 45. FIG. 5 shows the chestpiece 40 inserted into the case 20A.

The case 20A may be formed generally as a box or enclosure with front and back walls, left and right walls, a top wall, and an open bottom, thus enclosing the chestpiece on five sides. The front and back walls 22, 23 each have a midline vertical slot 24, 26 with an enlarged upper end 25 at the top wall, separating the front and back walls into left and right L, R portions. The front wall 22 and the back wall 23 may be spaced from the respective diaphragms 43, 45 to avoid transfer of contaminants to/from the diaphragms. The case may be made of heat tolerant material, for example an autoclavable plastic.

Figure 6A:
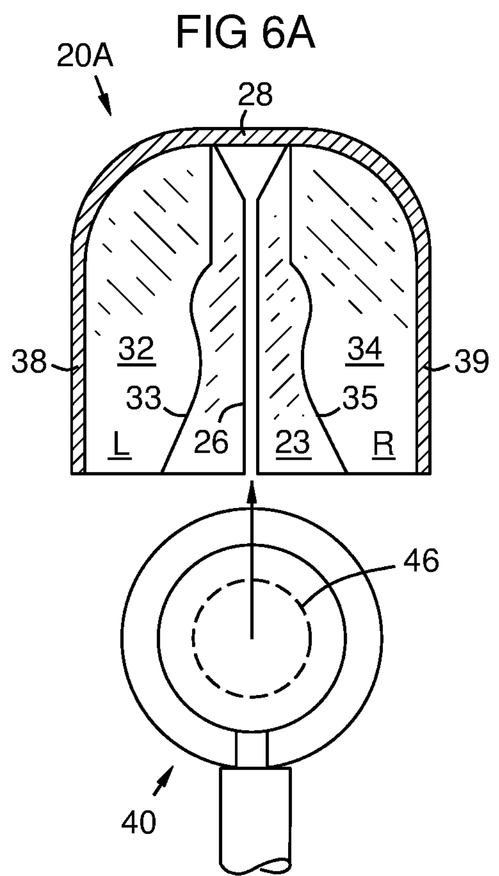
FIG. 6A is a sectional view taken on line 6-6 of FIG. 1 with an approaching chestpiece.
Figure 6B:
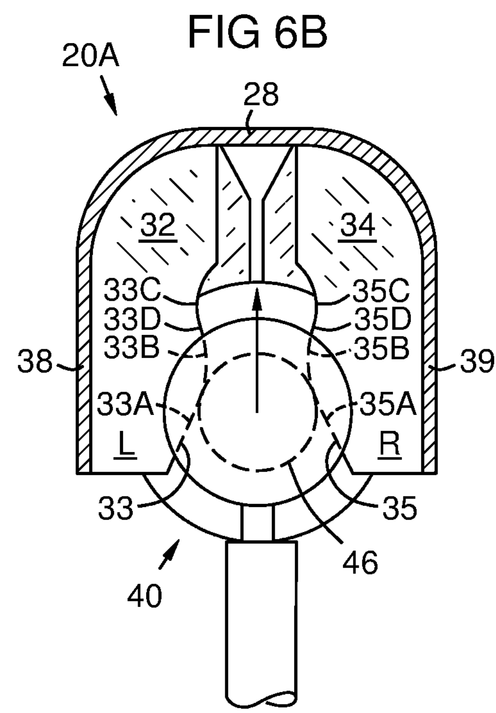
FIG. 6B is a sectional view taken on line 6-6 of FIG. 1 with a partly inserted chestpiece.
Figure 6C:
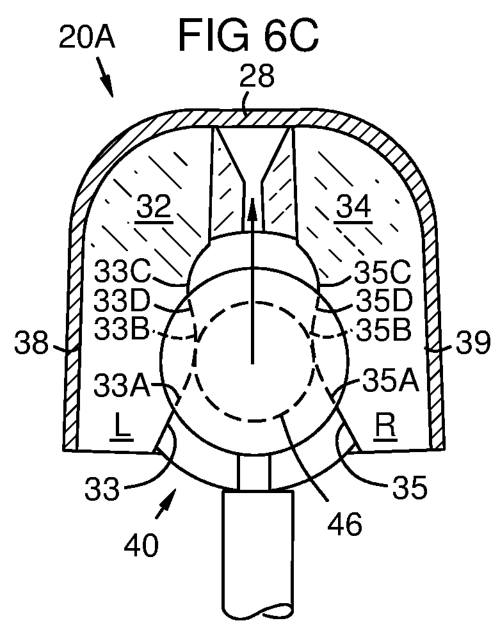
FIG. 6C is a sectional view taken on line 6-6 of FIG. 1 with a further inserted chestpiece.
Figure 6D:
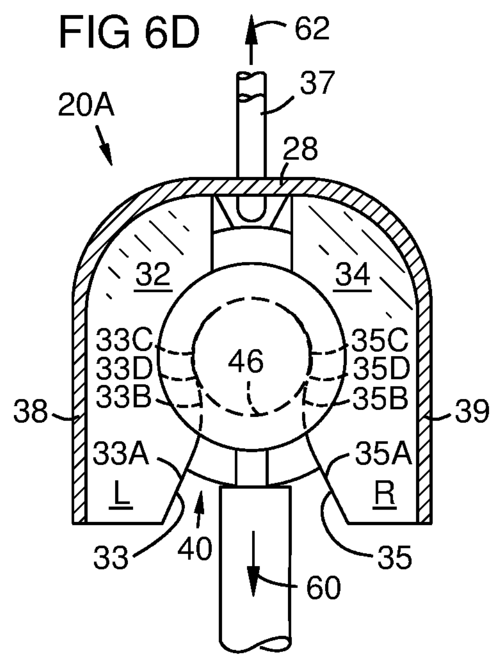
FIG. 6D is a sectional view taken on line 6-6 of FIG. 1 with a fully inserted chestpiece.

FIG. 6A is a sectional view of the case 20A taken on line 6-6 of FIG. 1 showing the left and right jaws 32, 34 attached to respective left and right side walls 38, 39 of the case. The jaws 32, 34 have respective opposed surfaces 33, 35 of varying separation that allow insertion, retention, and removal of the chestpiece 40. FIG. 6B shows the body 46 of the chestpiece 40 being pushed inward against an insertion ramp portion 33A, 35A of the opposed jaw surfaces 33, 35, which also have a waist portion 33B, 35B, a retention portion 33C, 35C, and a removal ramp portion 33D, 35D. This shape allows the chestpiece 40 to be inserted by pushing it inward against the insertion ramp 33A, 35A, causing the jaws to separate, with the top wall 28 acting as a hinge and spring. FIG. 6C shows the chestpiece 40 being pushed further inward. FIG. 6D shows the chestpiece fully inserted into the retention portion 33C, 35C of the jaw surfaces 33, 35. In this position, the jaws close enough to retain the body 46 of the chestpiece behind the waist 33B, 35B of the jaws. The spring aspect of the top wall may be relaxed in the retention position of FIG. 6D or it may clamp the retention portions 33C, 35C onto the chestpiece body if the retention portions are closer together in the relaxed position of the top wall than the diameter or diagonal of the chestpiece body. A lanyard 37 may be attached through the holes 30 seen in FIG. 1. The stethoscope can be pulled 60 out of the case 20A while retaining 62 the lanyard, for example by having the lanyard attached to a medical bag in which the stethoscope is carried or with the lanyard around a practitioner's neck. This gives instant access to the stethoscope, while retaining the case for quick re-insertion.

Figure 7:
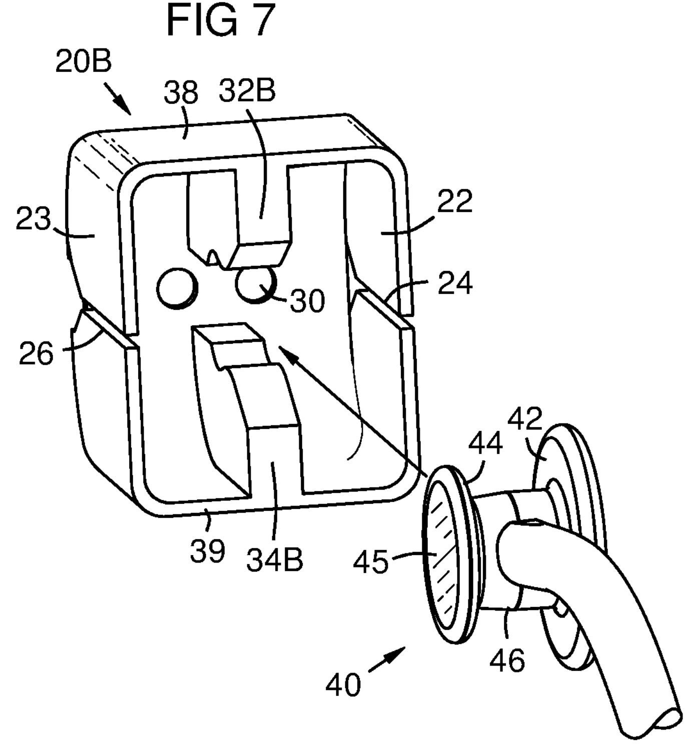
FIG. 7 is a perspective view of an embodiment with single-fin clamp jaws.

FIG. 7 shows a case 20B with jaws 32B, 34B formed as single fins. In an optional modular assembly embodiment, the jaws may be attached to the side walls during assembly. This allows the jaws to be interchangeable with other jaws for different types of stethoscopes while using the same case box part in the assembly process.

Figure 8:
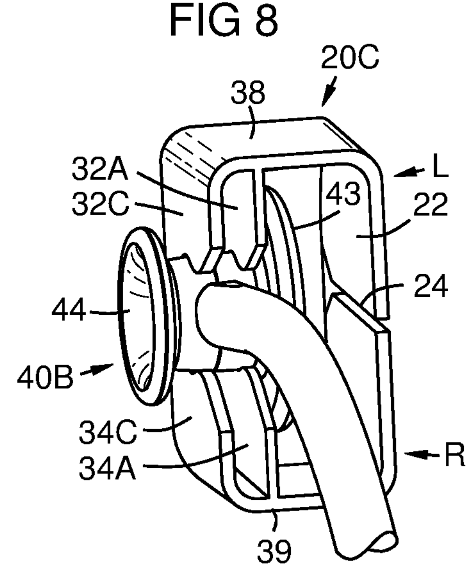
FIG. 8 is a perspective view of a one-sided embodiment.

FIG. 8 show a case 20C for a chestpiece 40B with a diaphragm 43 on one end, and a bell 44 without a diaphragm on the other end. Only the diaphragm end of this type of chest piece 40B is delicate, so one-sided protection is sufficient. However, a two-sided case 20A or 20B as previously shown can also be used for this chestpiece. In this embodiment 20C the left jaw is formed by one or more fins 32A, 32C and right jaw is formed by one or more fins 34A, 34C. There is no need for a back wall 23 as shown in previous embodiments 20A, 20B.

Figure 9:
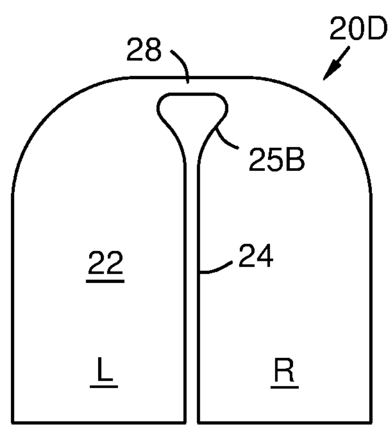
FIG. 9 is a front view of case with an alternate slot end shape.

FIG. 9 is a front view of a case 20D with a slot upper end enlargement 25B having a rounded base-up triangular shape that does not overlap the top wall 28.

Figure 10:
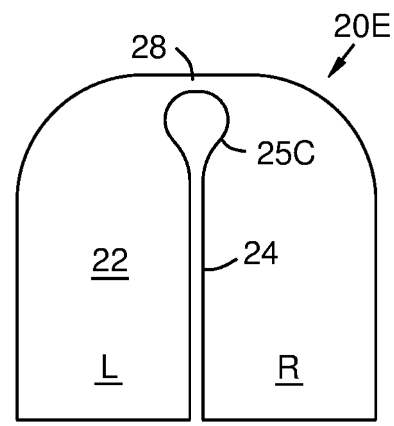
FIG. 10 is a front view of case with another slot end shape.

FIG. 10 is a front view of a case 20E with a slot upper end enlargement 25C that is bulb shaped and does not overlap the top wall 28.

In all embodiments, the case surrounds a stethoscope chestpiece in order to protect it from damage from outside forces. The case has a flexible top wall that allows internal fins to act in a claw-like clamping fashion in order to secure the chestpiece inside the case. The internal fins are shaped in a way that allows for fast insertion and removal of the chestpiece. When inserted, one or both bells of the chestpiece, depending on the embodiment, are surrounded on five sides to protect it/them from outside forces.

While various embodiments of the present invention have been shown and described herein, such embodiments are provided by way of example only. Variations and substitutions may be made by those skilled in the art without departing from the invention herein. Accordingly, the invention is to be limited only by the scope and intended meaning of the appended claims.

The invention claimed is:

1. A protective case for a stethoscope chestpiece, comprising:

an enclosure with an open bottom and first and second side walls hingedly interconnected by a flexible top wall;

first and second jaws extending inwardly towards each other from the first and second side walls respectively, the jaws being urged toward each other by the flexible top wall acting as a spring when the jaws are moved apart;

a front wall comprising first and second front wall portions attached to the first and second side walls respectively;

a first separation slot running from the top wall to the open bottom of the enclosure between the first and second front wall portions; and a first space between the jaws and the front wall that accommodates a first bell of a stethoscope chestpiece.

2. The protective case of claim 1, wherein the first and second jaws each comprise at least one fin extending inwardly from the first and second side walls respectively.

3. The protective case of claim 1, wherein the jaws comprise an open bottom end with converging insertion ramps that cause the jaws to part when a chestpiece body is pushed into the insertion ramps.

4. The protective case of claim 3, the jaws further comprising:

a waist with less separation between the jaws than a separation of the bottom end of the jaws; and a retention portion with greater separation between the jaws than at the waist;

wherein, upon insertion of the chestpiece body into the retention portion, the jaws retain the body of the chestpiece in the retention portion and hold the first bell thereof in the first space without the first bell contacting the front wall.

5. The protective case of claim 4 further comprising:

a back wall comprising first and second back wall portions attached to the first and second side walls respectively, the back wall separated into the first and second back wall portions by a second separation slot running from the top wall to the open bottom of the enclosure; and a second space between the jaws and the back wall, wherein upon insertion of the chestpiece body into the retention portion, the jaws retain the body of the chestpiece in the retention portion and hold a second bell of the chestpiece in the second space without the second bell contacting the back wall.

6. The protective case of claim 1, wherein the first separation slot comprises an enlargement at a top end thereof adjacent the top wall.

7. The protective case of claim 6, wherein the enlargement is shaped as a rounded base-up triangle or a bulb.

8. A protective case for a stethoscope chestpiece, comprising:

first and second pivotally separable case parts interconnected by a flexible top wall acting as a hinge and a spring that urges the two case parts toward each other when they are pivoted apart; and first and second opposed jaws attached within the two respective parts of the case;

wherein the jaws comprise respective opposed insertion ramps that move the jaws apart upon insertion of a chestpiece therein, a retention portion between the jaws that retains the chestpiece, and respective opposed removal ramps that move the jaws apart upon pulling of the chestpiece from the retention portion;

wherein the chest piece is inserted into the protective case by pushing it into the insertion ramps, and is removed by pulling it outward against the removal ramps; and wherein a first diaphragm of the chestpiece is protected within the case behind a front wall of the case.

9. The protective case of claim 8, further comprising a back wall that protects a bell or second diaphragm of the chestpiece opposite the first diaphragm thereof.

10. A protective case for a stethoscope chestpiece, comprising:

pivotally separable left and right case parts;

a top wall acting as a hinge between the left and right case parts;

front and back walls attached to the top wall, each of the front and back walls comprising left and right wall portions separated by a separation slot running from the top wall to an open bottom of the case; and left and right opposed jaws in the respective left and right parts of the case;

wherein the jaws comprise an open bottom end with converging insertion ramps that move the jaws apart when a chestpiece body is pushed into the ramps;

wherein the jaws further comprise opposed retention portions that retain the body of the chestpiece between the jaws with a bell of the chestpiece within the case;

wherein, the top wall acts as a spring allowing the left and right case parts and the jaws therein to elastically diverge to receive the chestpiece then close and hold it in the retention portions of the jaws.

11. The protective case of claim 10, wherein each of the separation slots comprises an enlarged upper end adjacent the top wall.

12. The protective case of claim 10, wherein each of the separation slots comprises an enlarged upper end adjacent the top wall, the enlarged upper end of each slot being shaped as a base-up triangle or a bulb.

* * * * *